United States Patent
Xue

(10) Patent No.: US 10,702,648 B2
(45) Date of Patent: Jul. 7, 2020

(54) FULLY-AUTOMATIC REGIONAL CITRATE ANTICOAGULATION MACHINE

(71) Applicant: Yingfeng Xue, Beijing (CN)

(72) Inventor: Yingfeng Xue, Beijing (CN)

( * ) Notice: Subject to any disclaimer, the term of this patent is extended or adjusted under 35 U.S.C. 154(b) by 303 days.

(21) Appl. No.: 15/567,535

(22) PCT Filed: Sep. 15, 2015

(86) PCT No.: PCT/CN2015/000643
§ 371 (c)(1),
(2) Date: Oct. 18, 2017

(87) PCT Pub. No.: WO2017/045088
PCT Pub. Date: Mar. 23, 2017

(65) Prior Publication Data
US 2018/0110916 A1    Apr. 26, 2018

(51) Int. Cl.
| A61M 1/36 | (2006.01) |
| A61M 1/14 | (2006.01) |
| A61M 1/16 | (2006.01) |
| G01N 1/14 | (2006.01) |
| G01N 1/34 | (2006.01) |
| G01N 33/49 | (2006.01) |
| A61B 5/00 | (2006.01) |

(52) U.S. Cl.
CPC ............ A61M 1/3675 (2013.01); A61M 1/14 (2013.01); A61M 1/1601 (2014.02); A61M 1/3609 (2014.02); G01N 1/14 (2013.01); G01N 1/34 (2013.01); G01N 33/49 (2013.01); G01N 33/492 (2013.01); *A61B 5/4839* (2013.01); *A61B 5/6866* (2013.01); *A61M 1/3626* (2013.01); *A61M 1/3627* (2013.01); *A61M 2205/50* (2013.01)

(58) Field of Classification Search
CPC .............. A61M 1/3675; A61M 1/1601; A61M 1/3609; A61M 1/14; G01N 1/14; G01N 1/34; G01N 33/49; G01N 33/492
See application file for complete search history.

(56) References Cited

U.S. PATENT DOCUMENTS

| 2007/0066928 A1* | 3/2007 | Lannoy | A61M 1/16 604/6.07 |
| 2013/0315780 A1* | 11/2013 | Cook | G01N 21/66 422/52 |

* cited by examiner

*Primary Examiner* — Ariana Zimbouski
(74) *Attorney, Agent, or Firm* — Egbert, McDaniel & Swartz, PLLC

(57) ABSTRACT

A fully-automatic regional citrate anticoagulation machine is disclosed. A sampling portion extracts a blood sample on line and in real time and sends it to a storage purifier for storage and purification. A sample injection portion conveys the blood sample in the blood sample storage purifier to a sample loading slot through a sample injection tube. An assay and analysis portion conveys, through a sample suction tube, the blood sample to an analyzer for blood sample assay and analysis. The sampling portion, the sample injection portion, the assay and analysis portion and an administration portion are connected to the program control portion. The program control portion controls, according to an internally-set program, operation of the sampling portion, the sample injection portion and the assay and analysis portion, and sends an instruction to the administration portion according to the data result obtained by the assay and analysis portion.

8 Claims, 5 Drawing Sheets

FULLY-AUTOMATIC REGIONAL CITRATE ANTICOAGULATION MACHINE

TECHNICAL FIELD

The invention relates to the technical field of medical instruments, in particular to a full-automatic regional citrate anticoagulation machine.

BACKGROUND

Continuous renal replacement therapy (CRRT), also known as continuous blood purification (CBP), is a new blood purification method. In 1995, the first International Conference on Continuous Renal Replacement Treatment recommended the use of a continuous 24-hour or near 24-hour continuous blood purification therapy to replace the purification method for the damaged kidney function, that is, continuous renal replacement therapy. Continuous renal replacement therapy includes continuous arteriovenous, continuous veno-venous hemofiltration (CAVH, CVVH), continuous arteriovenous, veno-venous hemodialysis (CAVDH, CVVDH), and continuous arteriovenous, veno-venous hemodiafiltration (CAVHDF, CVVHDF).

Hemodialysis refers to drawing the blood out of the body to remove metabolic wastes and impurities in the blood through the osmotic membrane of the hemodialysis machine, and then transporting the purified blood back into the body, which is commonly known as "kidney cleansing" and "blood cleansing". Hemodialysis can be used for renal failure patients, or those with blood poisoning but other bodies cannot discharge the toxic substances themselves. The blood in the body is drained to the outside, and through a dialyzer composed of numerous hollow fibers, the blood and electrolyte solution similar to the organic concentration (dialyzate) have material exchange via dispersion/convection inside and outside hollow fibers, to remove the metabolic wastes in the body and maintain electrolyte and acid-base balance; and remove excess water in the body.

If the continuous renal replacement therapy or hemodialysis treatment therapy is needed by the patients in the event of active bleeding, recent major surgery, severe trauma, coagulation dysfunction and other high-risk bleeding conditions, anticoagulation is to ensure that this treatment is one of the basic conditions for the smooth progress of this treatment when performing this blood purification treatment. At present, regional citrate anticoagulation (RCA), i.e., RCA-CRRT and RCA-HD, is mostly used. The principle is as follows: continuous input of sodium citrate solution is made when the human blood is led out, in which case the calcium ion in the sodium citrate chelate blood generates soluble complex calcium citrate that is difficult to dissociate, to reduce the calcium ion in the blood, prevent prothrombin conversion into the thrombin, so as to achieve the role of anticoagulation; when the extracorporeal blood enters into the body, the calcium ion solution is re-entered to reach the normal level of the human body and restore the body coagulation mechanism.

But at the current stage, the use of RCA method is still with more manual operation: manual calculation of the initial dosage—manual administration—manual blood drawing—manual test of electrolyte and other indicators (delay the time for adjusting dosage of administration)—manual calculation of the dosage—manual adjustment of the dosage metering. The manual process must be repeated once every 1-4 hours. In the time interval of one RCA treatment that lasts for several hours to dozens of hours, the above manual process must be repeated several times, which is cumbersome and time-consuming. Recently, some blood purification devices reduce the manual operation steps and can automatically input the citrate salt anticoagulant, but the input volume and speed still need to be manually adjusted and controlled, and it is necessary for separate blood collection and analysis. Moreover, the current clinical use cost of RCA therapy is high, with cumbersome operation, which restricts the clinical promotion of RCA. Currently, only about 10% of the patients or the wounded needing this therapy has the opportunity to receive this treatment.

SUMMARY

The embodiment provides a full-automatic regional citrate anticoagulation machine, to solve the technical problems of high expense and tedious and time-consuming operation steps due to mostly with manual operation or with partial manual operation in RCA methods of the prior art.

In order to solve the above problem, the present invention discloses a full-automatic regional citrate anticoagulation machine, comprising a sampling portion, a sample injection portion, an assay and analysis portion, an administration portion, and a program control portion, wherein the sampling portion comprises a connecting catheter, an air detector, a pressure sensor I, a peristaltic pump I and a blood sample storage purifier that are successively connected in series; the sampling portion extracts a blood sample on line and in real time and sends the blood sample to a blood sample storage purifier for storage and purification; the sample injection portion comprises a peristaltic pump a sample injection tube and a sample loading slot, the first end of the peristaltic pump II is communicated with the peristaltic pump I, the second end of the peristaltic pump II is communicated with the sample injection tube, the sample injection tube is inserted into the sample loading slot, the sample injection portion conveys the blood sample in the blood sample storage purifier to a sample loading slot through a sample injection portion channel; the assay and analysis portion comprises a sample suction tube and an analyzer, one end of the sample suction tube is inserted in the sample loading slot and the other end is connected to the analyzer, the sample suction tithe conveys the blood sample in the sample loading slot to an analyzer for blood sample analysis; the sampling portion, the sample injection portion and the assay and analysis portion are connected to the program control portion; the program control portion controls, according to an internally-set program, operation of the sampling portion, the sample injection portion and the assay and analysis portion, compares the data results obtained by the analyzer and sends an instruction to the administration portion according to the comparison result.

Preferably, the administration portion comprises a first connecting tube, one end of the first connecting tube is connected with an arterial-end line inlet on the treatment device, the other end is connected with a program-controlled infusion pump, the citrate solution enters into the arterial-end line via the first connecting tube through the program-controlled infusion pump; the administration portion further comprises a second connecting tube, one end of the second connecting tube is connected with a venous-end line inlet on the treatment device, the other end is connected with the program-controlled infusion pump, and the calcium enters into the arterial-end line via the second connecting tube through the program-controlled infusion pump.

Preferably, the connecting catheter of the sampling portion comprises a body peripheral venous connection catheter for sucking and spitting blood samples online, an arterial line connecting catheter on the treatment device, and a venous line connecting catheter on the treatment device; the connecting catheters are connected on the passage of the sampling portion through two-position three-way valves and communicated with the air detector, and the front end of the air detector is also provided with cut-off clamp I; a cut-off clamp II is also provided between the pressure sensor I and the peristaltic pump II; the blood sample storage purifier is also internally connected with a pressure sensor II and a standard liquid bottle, a cut-off clamp III is provided between the blood sample storage purifier and the pressure sensor II, the standard liquid bottle is provided with a standard liquid and acts with the pressure sensor II to clean the passage of the sampling portion.

Preferably, the sample injection portion is communicated with the blood sample storage purifier of the sampling portion, such three parts are communicated by setting two-position three-way valve between the pressure sensor I, peristaltic pump I and peristaltic pump II, and the two-position three-way valve is also connected with a liquid and gas removal pump.

Preferably, the sample injection portion further comprises a residual blood, standard liquid collector and a sample injection tube cleaning utensil for online sample blood supply, wherein the residual blood, standard liquid collector and the sample injection tube cleaning utensil for online sample blood supply are connected in the sample injection portion through manipulator, and the line of the sample injection portion for online sample blood supply is washed by the instructions issued by the program control portion.

Preferably, the program control portion comprises a computer and a PLC.

Preferably, the analyzer carries out online monitoring for one or more indicators in electrolytes, blood glucose, parathyroid hormone, adrenal hormone, PH value and citrate concentration.

Preferably, the program control portion decides the administration state of the administration portion according to the comparison operation result between the sample blood analysis data of the analyzer and the basic data set by the program.

Preferably, the program control portion sets the basis data and the analyzer analyzes the sample blood data to control the program-controlled infusion pump of the citrate solution and the program-controlled injection pump of calcium within the basic data range to implement the specific administration state; when the sample blood analysis data of the analyzer is higher than the program setting data, the program control portion will automatically adjust the administration state of calcium down-regulation or the administration state of citrate solution up-regulation; when the sample blood analysis data of the analyzer is lower than the program setting data, the program control portion will automatically adjust the administration state of calcium up-regulation or the administration state of citrate solution down-regulation.

The full-automatic regional citrate anticoagulation machine provided by the present invention comprises a sample injection portion, a sample injection portion, an assay and analysis portion, an administration portion and a program control portion. Under the control of the program control portion, the sampling portion automatically absorbs blood samples and the sample injection portion injects the collected blood samples into the sample loading slot, so as to analyze the blood sample through the assay and analysis portion, the analysis data is transmitted to the program control portion, and the program control portion compares the analysis data with the basic data set by the program, so as to adjust the administration state of the administration portion. The full-automatic regional citrate anticoagulation machine provided by the present invention completely substitutes manual calculation of the initial dosage—manual administration—manual blood drawing—manual test of electrolyte and other indicators—manual calculation of the dosage—manual adjustment of the dosage metering, to avoid the time-consuming manual operation to delay the time for adjusting the dosage, and release the health care workers from the cumbersome labor work to increase the efficiency of medical care resources and the hospital; the full-automatic regional citrate anticoagulation machine provided by the present invention monitors the corresponding required indicator data online in real time, which does not need manual blood drawing and laboratory monitoring, saving valuable treatment adjustment time; it automatically analyzes the monitoring results data and automatically adjusts the rate of administration, so that the old experts do not need to control and calculate the rate of administration to simplify the complex treatment methods, which helps the rapid promotion of RCA technology, thus more patients get treatment opportunities in addition, the RCA treatment costs are significantly lowered, and a new era for on-line real-time monitoring of the electrolyte, sugar, parathyroid hormone, adrenal hormone, PH value and citrate concentration is opened up.

BRIEF DESCRIPTION OF THE DRAWINGS

By reading detailed description of the preferred implementations below, various other advantages and benefits will become clear for an ordinary person skilled in the art. The drawings are for the purpose of illustrating preferred embodiments only, but not to limit the present invention. And throughout the drawings, the same reference numerals denote the same parts. In the drawings.

Callouts: 1. body peripheral venous connection catheter, 2. arterial line connecting catheter on the treatment device, 3. venous line connecting catheter on the treatment device, 4. two-position three-way valve, 5. two-position three-way valve, 6. cut-off clamp I, 7. air detector, 8. pressure sensor I, 9. two-position three-way valve, 10. peristaltic pump I, 11. manipulator, 12. sample injection tube for online blood sample supply, 13. sample suction tube, 14. analyzer, 15. program control portion, 16. program-controlled infusion pump, 17. program-controlled injection pump, 18. first connecting tube, 19 second connecting tube, 20. cut-off clamp II, 21. peristaltic pump II. 22. blood sample storage purifier, 23. cut-off clamp III, 24. pressure sensor II, 25. standard liquid bottle, 26. liquid and gas removal pump, 27. residual blood and standard liquid collector, 28. cleaning utensil for sample injection tube for online sample blood supply, 29. citrate liquid bottle, 30. sample loading slot.

DETAILED DESCRIPTION

Hereinafter, the present invention will be described in detail with reference to the accompanying drawings and in combination with the embodiments. It should be noted that the features in the embodiments and the embodiments of the present invention may be combined with each other in a non-conflicting situation.

Embodiment 1

Figure 1:
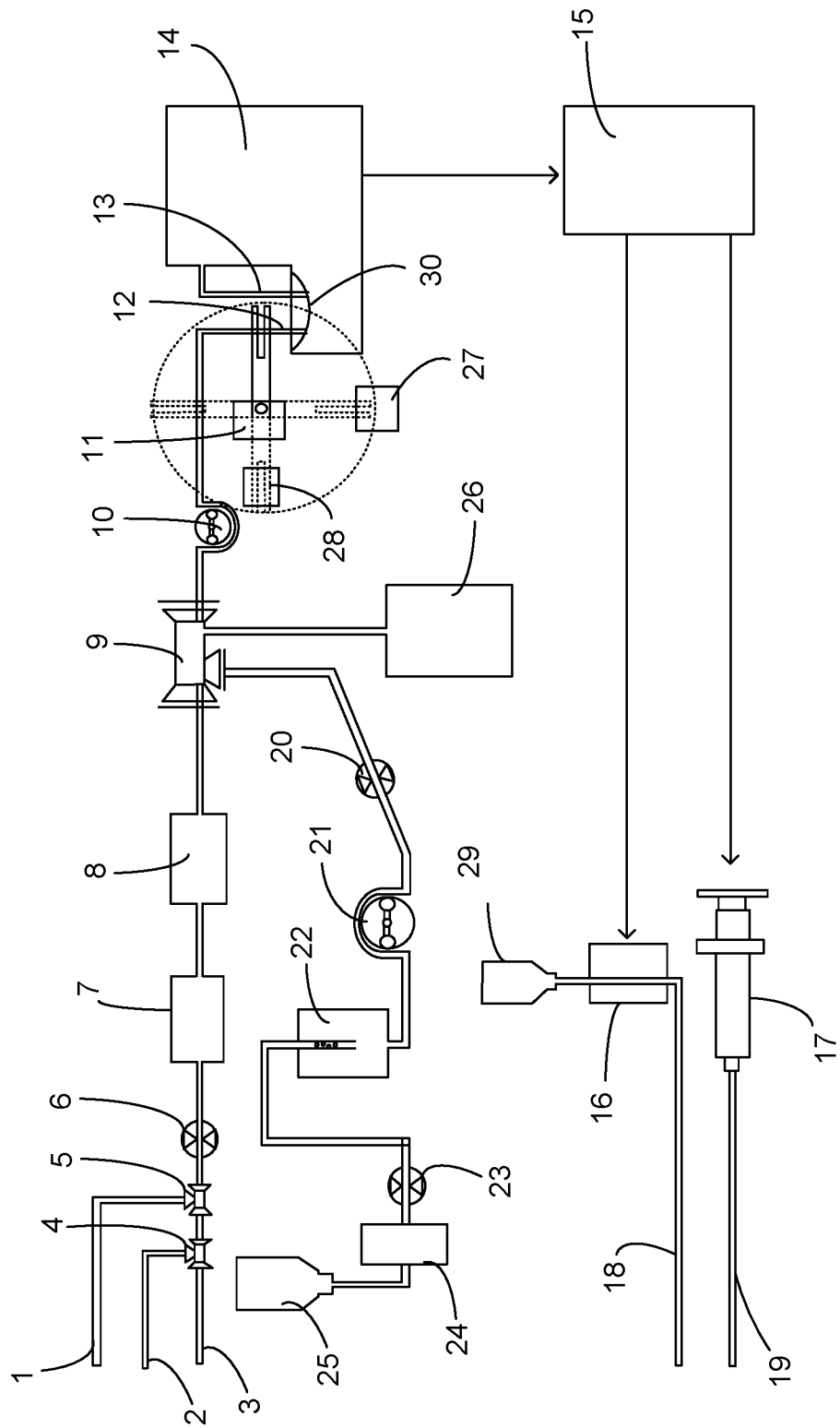
FIG. 1 illustrates the overall connection relations of the full-automatic regional citrate anticoagulation machine in the present invention.

As shown in FIG. 1, this embodiment discloses a full-automatic regional citrate anticoagulation machine, comprising a sampling portion, a sample injection portion, an assay and analysis portion, an administration portion, and a program control portion, wherein the sampling portion comprises a connecting catheter, an air detector 7, a pressure sensor I 8, a peristaltic pump I 10 and a blood sample storage purifier 22 that are successively connected in series; the sampling portion extracts a blood sample on line and in real time and sends the blood sample to a blood sample storage purifier 22 for storage and purification; the sample injection portion comprises a peristaltic pump II 21, a sample injection tube, i.e., a sample injection tube 12 for online sample blood supply, and a sample loading slot 30, the first end of the peristaltic pump II 21 is communicated with the peristaltic pump I 10, the second end of the peristaltic pump II 21 is communicated with the sample injection tube 12 for online sample blood supply, the sample injection tube 12 for online sample blood supply is inserted into the sample loading slot 30, the sample injection portion conveys the blood sample in the blood sample storage purifier 22 to a sample loading slot 30 through a sample injection portion channel; the assay and analysis portion comprises a sample suction tube 13 and an analyzer 14, one end of the sample suction tube 13 is inserted in the sample loading slot 30 and the other end is connected to the analyzer 14, the sample suction tube 13 conveys the blood sample in the sample loading slot 30 to an analyzer 14 for blood sample analysis; the sampling portion, the sample injection portion and the assay and analysis portion are connected to the program control portion 15; the program control portion 15 controls, according to an internally-set program, operation of the sampling portion, the sample injection portion and the assay and analysis portion, compares the data results obtained by the analyzer 14 and sends an instruction to the administration portion according to the comparison result.

As shown in FIGS. 2 to 7, the connecting catheter is connected to the blood purifier, and the administration portion is administered with the basic data set by the program control portion 15. Under the control of the program control portion 15, the sampling portion sets the cycle for blood sample collection, and the blood sample enters into the blood sample storage purifier 22 for storage and purification successively through the connecting catheter, the air detector 7, the pressure sensor I 8 and the peristaltic pump I 10, and the sample injection portion takes the sample blood in the blood sample storage purifier 22. The blood sample enters into the peristaltic pump I 10 through the peristaltic pump II 21, and is then fed into the sample loading slot 30 by the sample injection tube 12 for online sample blood supply; the sample suction tube 13 of the analyzer draws blood from the sample loading slot 30 for analysis by the analyzer 14 to derive the data of the required analysis. Later, the program control portion 15 compares the analysis data with the set basic data, and adjusts the administration state of the administration portion based on the comparison result. After sampling and sample injection, the excess blood can be returned to the blood purification machine through the circuit, and then the passages of the sampling portion and the sample injection analysis portion will be subject to automatic cleaning. During the course of treatment, sampling, injection, administration adjustment, cleaning and other processes can be set with cycle and frequency as required, but also the blood sample can be subject to a variety of indicator analysis if necessary. Full automatic processing not only can timely and effectively adjust the administration state, improve work efficiency, but also can eliminate the complex operating procedures, reduce labor costs, and better utilize health care resources.

Embodiment 2

This embodiment provides a full-automatic regional citrate anticoagulation machine. On the basis of Embodiment 1, the administration portion comprises a first connecting tube 18, one end of the first connecting tube 18 is connected with an arterial-end line inlet on the treatment device, the other end is connected with a program-controlled infusion pump 16, the citrate solution enters into the arterial-end line via the first connecting tube 18 through the program-controlled infusion pump 16; the administration portion further comprises a second connecting tithe 19, one end of the second connecting tube 19 is connected with a venous-end line inlet on the treatment device, the other end is connected with the program-controlled infusion pump 17, the calcium enters into the arterial-end line via the second connecting tube 19 through the program-controlled infusion pump 17. The citrate solution in the citrate solution bottle 29 is delivered to the arterial-end line through the program-controlled infusion pump 16. The program control portion 15 compares the blood sample analysis data obtained by the analyzer 14 with the basic data set by the program control portion 15, and adjusts the administration state of the citrate solution and the calcium in the administration portion according to the comparison result, including the rate of administration and the dosage, as well as mixing proportion of the two.

Embodiment 3

This embodiment provides a full-automatic regional citrate anticoagulation machine. As shown in FIG. 1, on the basis of Embodiment the connecting catheter of the sampling portion comprises a body peripheral venous connection catheter 1 for sucking and spitting blood samples online, an arterial line connecting catheter 2 on the treatment device, and a venous line connecting catheter 3 on the treatment device; the connecting catheters are connected on the passage of the sampling portion through two-position three-way valves (4, 5) and communicated with the air detector 7, and the front end of the air detector 7 is also provided with cut-off clamp I 6; a cut-off clamp 20 is also provided between the pressure sensor I 8 and the peristaltic pump II 21; the blood sample storage purifier 22 is also internally connected with a pressure sensor II 24 and a standard liquid bottle 25, a cut-off clamp III 23 is provided between the blood sample storage purifier 22 and the pressure sensor II 24, the standard liquid bottle 25 is provided with a standard liquid and acts with the pressure sensor II 24 to clean the passage of the sampling portion. When connecting the CRRT mode, the arterial line connecting catheter 2 is connected to the arterial line of the blood purification engine, the venous line connecting catheter 3 is connected to the venous line of the blood purifier; under this mode, the full-automatic regional citrate anticoagulation machine will automatically choose sucking and spitting blood samples in the arterial and venous lines of extracorporeal circulation for automatic detection. When connecting to HD mode, body peripheral venous connection catheter 1 is connected to the body peripheral veins, venous line connection catheter 3 is connected with the venous line of the blood purifier; under this mode, the full-automatic regional citrate anticoagulation machine will automatically choose sucking and spitting blood samples in the body peripheral veins and venous line of extracorporeal circulation for automatic detection. The full-automatic regional citrate anticoagulation machine provided by the present invention applies CRRT mode or HD mode for treatment as needed.

Embodiment 4

Figure 2:
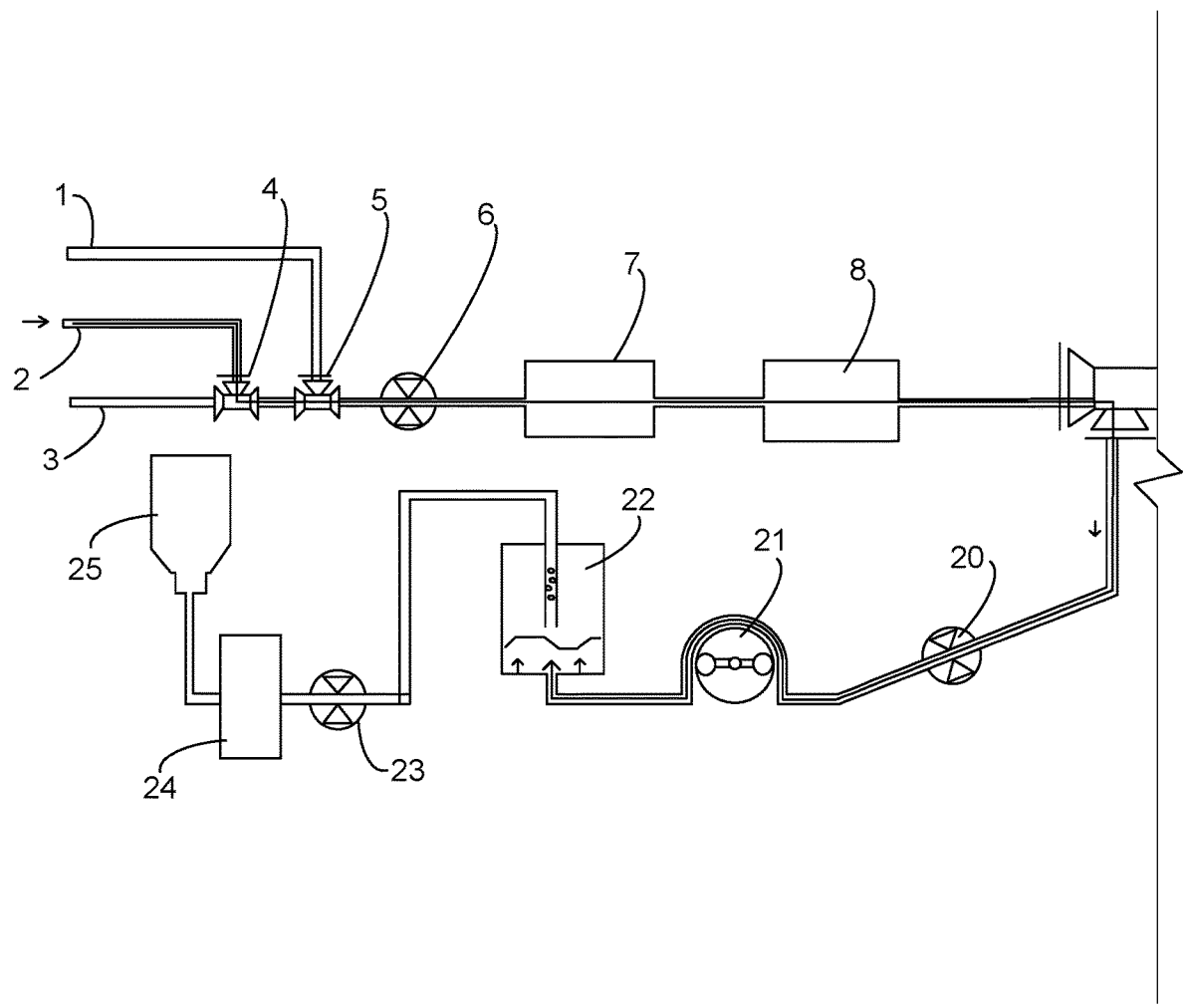
FIG. 2 illustrates a sampling passage of the sampling portion of the full-automatic regional citrate anticoagulation machine in the present invention.
Figure 3:
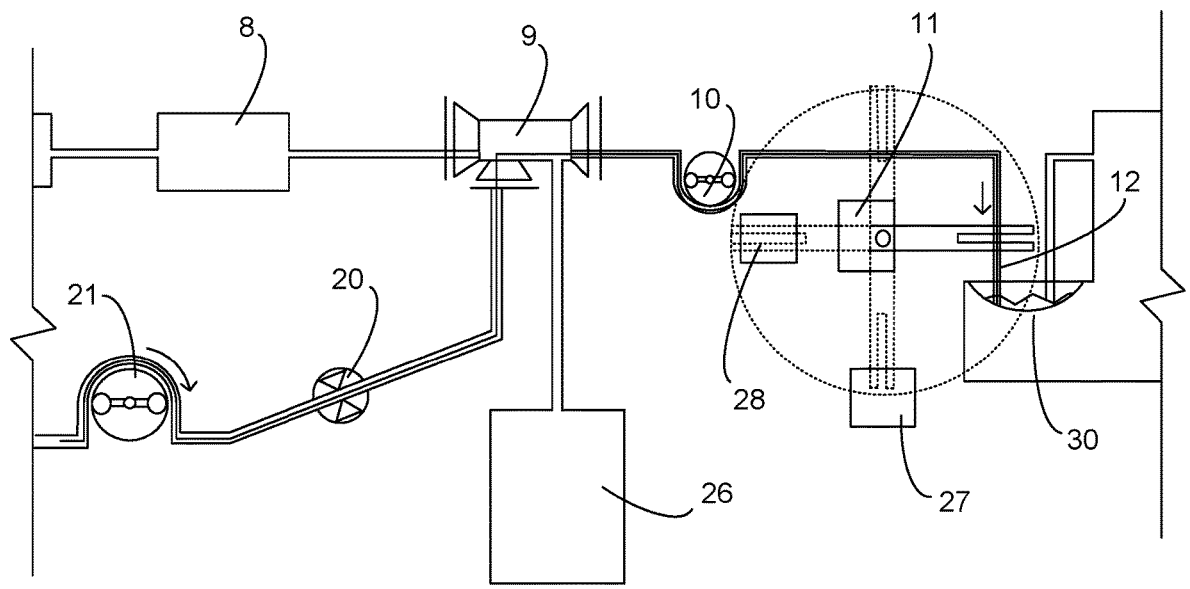
FIG. 3 illustrates a sample injection passage of the sample injection portion of the full-automatic regional citrate anticoagulation machine in the present invention.
Figure 4:
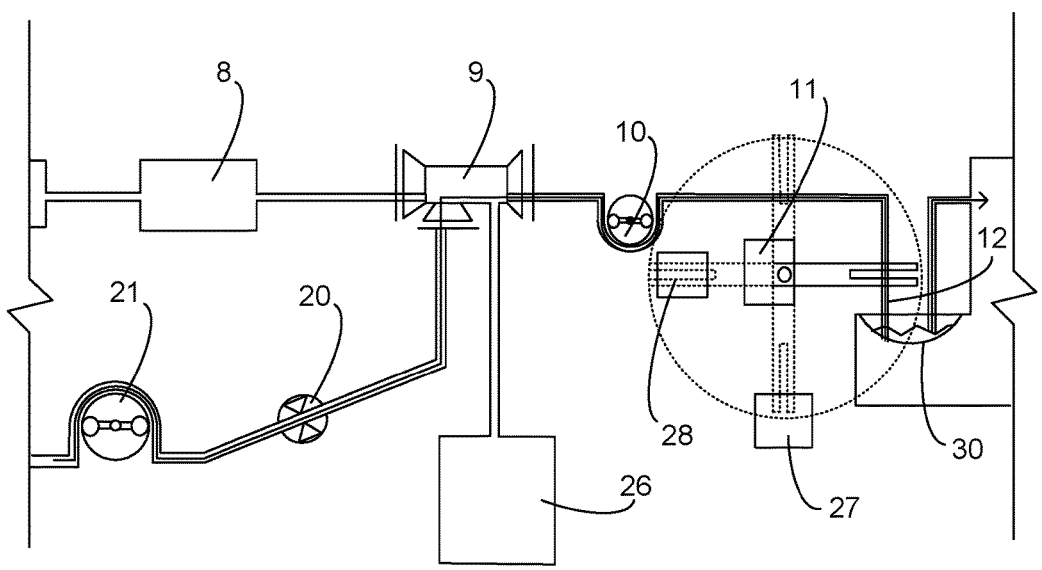
FIG. 4 illustrates an analytical passage of the assay and analysis portion of the full-automatic regional citrate anticoagulation machine in the present invention.

This embodiments provides a full-automatic regional citrate anticoagulation machine, wherein on the basis of the Embodiment 1, the sample injection analysis portion is communicated with the blood sample storage purifier 22 of the sampling portion, such three parts are communicated by setting two-position three-way valve 9 between the pressure sensor I 8, peristaltic pump I 10 and peristaltic pump II 21, and the two-position three-way valve 9 is also connected with a liquid and gas removal pump 26. As shown in FIG. 2, the flow direction is changed through the two-position three-way valve 9 to form a sampling portion passage, that is, to automatically draw blood samples through the arterial line connecting catheter 2, and the blood samples pass through the two-position three-way valve 4, two-position three-way valve 5 (change the flow direction), open cut-off clamp I 6, air detector 7 and pressure sensor I 8 and two-position three-way valve 9 (change the flow direction), open cut-oft clamp II 20 and peristaltic pump II 21 to go into the blood sample storage purifier 22, preparing for the next sample blood injection. As shown in FIGS. 3 and 4, the flow direction is changed by the two-way three-way valve 9 to form a sample injection analysis portion passage, that is, the blood sample in the blood sample storage purifier 22 passes through the peristaltic pump II 21, the open cut-off clamp II 20, and the two-way three-way valve 9 for flow direction change, and the peristaltic pump I 10, and is injected into the sample loading slot 30 by the sample injection tube 12 for online sample blood supply. The analyzer 14 sucks the blood sample through the sample suction tube 13 of the analyzer and analyze the data for real-time display; the data is transmitted to the program control portion 15.

Embodiment 5

Figure 5:
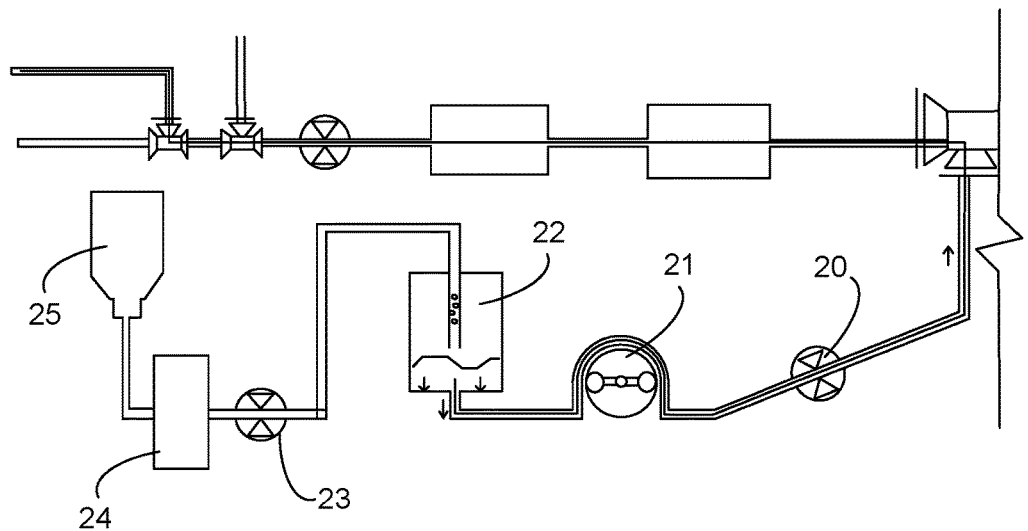
FIG. 5 illustrates a regurgitation path of the sampling portion of the full-automatic regional citrate anticoagulation machine in the present invention.
Figure 6:
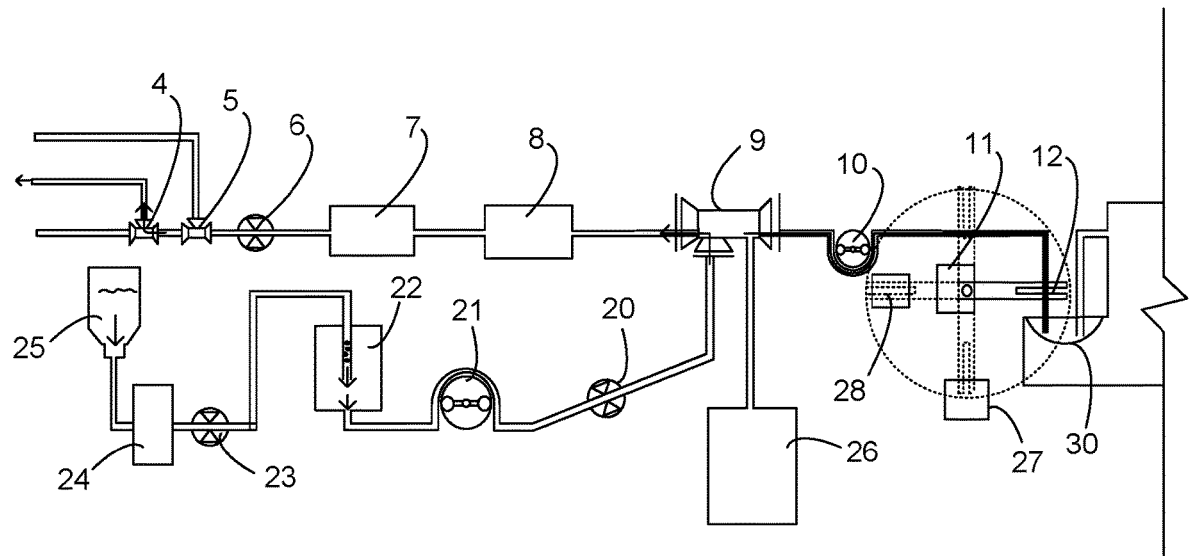
FIG. 6 illustrates a cleaning circuit of the sampling portion of the full-automatic regional citrate anticoagulation machine in the present invention.
Figure 7:
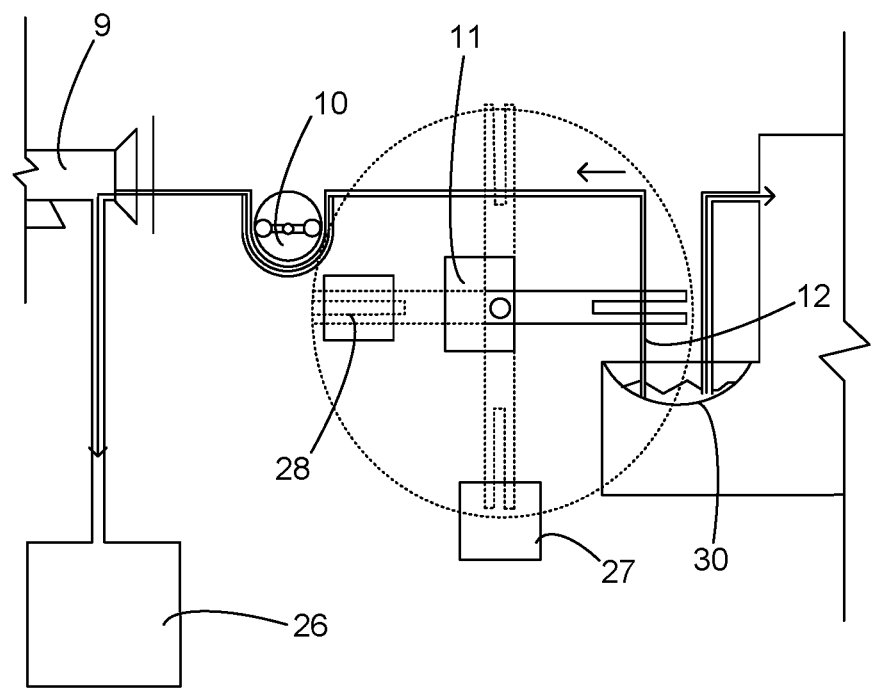
FIG. 7 illustrates a cleaning circuit of the sample injection portion of the full-automatic regional citrate anticoagulation machine in the present invention.

This embodiment provides a full-automatic regional citrate anticoagulation machine, wherein on the basis of Embodiment 1, the sample injection portion further comprises a residual blood, standard liquid collector 27 and a sample injection tube cleaning utensil 28 for online sample blood supply, wherein the residual blood, standard liquid collector 27 and the sample injection tube cleaning utensil 28 for online sample blood supply are connected in the sample injection analysis portion through the manipulator 11, and the line of the sample injection tube 12 for online sample blood supply and the sample suction tube 13 of the analyzer is washed by the instructions issued by the program control portion 15. As shown in FIGS. 5-7, for the full-automatic regional citrate anticoagulation machine provided in the present invention, the residual blood is automatically driven to return into the arterial and venous lines of the blood purification machine according to the program. When all the blood is returned, the standard solution in the standard bottle 25 continues to reflow until the line is cleaned to be without blood sample residue. The liquid and gas removal pump 26, the peristaltic pump I 10, and the sample injection tube 12 for online sample blood supply, sample suction tube 13 of the analyzer, analyzer 14, manipulator 11, residual blood, standard liquid collector 27, and cleaning utensil 28 for sample injection tube for online sample blood supply start automatic operation procedure to clean the sample injection tube 12 for online sample blood supply and the sample suction tube 13 of the analyzer. After cleaning, the sampling portion and the sample injection analysis portion are in standby status to wait for the next blood taking analysis.

Optionally, the program control portion of the full-automatic regional citrate anticoagulation machine provided in the present invention refers to computer and PLC. It is possible to control the sampling, sample injection, analysis, administration state and line cleaning procedures of the full-automatic regional citrate anticoagulation machine.

Optionally, for the full-automatic regional citrate anticoagulation machine provided in the present invention, analyzer shall be used to analyze the blood samples, and the analysis indicators include one or more of electrolyte of the blood sample, blood glucose, parathyroid hormone, adrenal hormone, PH value and citrate concentration, and in addition, online monitoring shall be made simultaneously.

Taking CRRT mode for example, the work process of the full-automatic regional citrate anticoagulation machine provided in the present invention is divided into two stages, in which the first process includes online real-time blood sampling, analysis, and real-time analysis of data transmission, and the second process involves the program-controlled intelligent administration.

The first process includes the following seven steps:

(1) Automatic cleaning: sample injection tube 12 for online sample blood supply, wherein the peristaltic pump 10, the sample injection tube 12 for online sample blood supply and the liquid, gas removal pump 26 work together;

(2) Arterial line connecting catheter 2 automatically absorbs blood samples: The blood passes through the two-position three-way valve 4, two-position three-way valve 5 (change the flow direction), open cut-off clamp I 6, air detector 7 and pressure sensor 8 and two-position three-way valve 9 (change the flow direction), open cut-off clamp II 20 and peristaltic pump II 21 to go into the blood sample storage purifier 22, preparing for the next sample blood injection;

(3) Blood sample ejection: The blood sample in the blood sample storage purifier 22 passes through the peristaltic pump II 21, the open cut-off clamp II 20, the two-way three-way valve 9 (change the flow direction) and the peristaltic pump I 10, and is injected into the sample loading slot 30 by the sample injection tube 12 for online sample blood supply;

(4) Analysis of blood samples: The analyzer 14 draws blood samples and analyzes the data and displays the data in real time, and then the data is transmitted to the program control portion 15;

(5) Regurgitation of residual blood samples in the main line along the original path: The anti-coagulation machine will, according to the program, automatically drive the residual blood to return, to the arterial and venous lines of the blood purification machine along the original path. When all the blood is returned, the standard liquid will continue the backflow until the line is cleaned without blood sample residue;

(6) Automatic cleaning of sample injection tube 12 for online sample blood supply and sample suction tube 13 of the analyzer: The liquid and gas removal pump 26, the peristaltic pump I 10, and the sample injection tube 12 for online sample blood supply, sample suction tube 13 of the analyzer, analyzer 14, manipulator 11, residual blood, standard liquid collector 27, and cleaning utensil 28 for sample injection tube for online sample blood supply start automatic operation procedure to clean the sample injection tube 12 for online sample blood supply and the sample suction tube 13 of the analyzer. After cleaning, the sampling portion and the sample injection analysis portion are in standby status to wait for the next blood taking analysis.

(7) After repeating the procedures (1) (2), (3), (4), (5), (6) in the first process by sucking and spitting sample blood by the venous line connecting catheter 3 of the blood purification machine, the analyzer 14 transmits the data to the program control portion 15, and then proceeds to the second stage, in which the program control portion 15 processes the data and issues an instruction to adjust the program-controlled infusion pump 16 and the program-controlled injection pump 17 to change the dosage.

In the second stage, program-controlled intelligent, administration includes a variety of processes, such as setting the corresponding database with different time interval and the initial measurement according to different weight levels. When the flow rate of the blood pump is different, different mathematical models can be utilized to calculate different databases, etc. Now the following six groups of procedures are taken as an example: each group of process has multiple echelons, such as the concentration value of multiple echelons, while a number of corresponding instructions are made. Taking the program database of the following two echelons for example:

(1) When the first laboratory analysis data falls within the basic data range, the program control portion 15 will issue an operation maintenance signal to the program-controlled infusion pump 16 and the program-controlled infusion pump 17;

This program database:
$1.1 \times 0.96 <$ calculated value of free calcium concentration in peripheral venous blood (mmol/L)$< 1.3 \times 0.96$, wherein the pump speed instruction of the program-controlled infusion pump 17 is 0, that is, keeping the original rate, and the rate instruction of the program-controlled infusion pump 16 is 0, i.e., keeping the original rate;

$0.2 <$ default free calcium concentration in the venous line blood of the blood purification machine (mmol/L)$< 0.35$, wherein the pump speed instruction of the program-controlled infusion pump 17 is 0, that is, keeping the original rate, and the rate instruction of the program-controlled infusion pump 16 is 0, i.e., keeping the original rate.

(2) When the first laboratory analysis result is higher than the basic data range, the program control portion 15 will send an instruction the program-controlled injection pump 17 to reduce the corresponding calcium supply rate;

This program database:
$1.3 \times 0.96 <$ calculated value of free calcium concentration in peripheral venous blood (mmol/L)$< 1.4 \times 0.96$, wherein the pump speed instruction of the program-controlled infusion pump 17 is to reduce 12.5%, and the rate instruction of the program-controlled infusion pump 16 is 0, i.e., keeping the original rate;

$0.2 <$ default free calcium concentration in the venous line blood of the blood purification machine (mmol/L)$< 0.35$, wherein the pump speed instruction of the program-controlled infusion pump 17 is 0, and the rate instruction of the program-controlled infusion pump 16 is 0, i.e., keeping the original rate.

(3) When the first laboratory analysis result is lower than the basic data range, the program control portion 15 will send an instruction the program-controlled injection pump 17 to increase the corresponding calcium supply rate;

This program database:
$0.9 \times 4.96 <$ calculated value of free calcium concentration in peripheral venous blood (mmol/L)$< 1.1 \times 0.96$, wherein the pump speed instruction of the program-controlled infusion pump 17 is to increase 12.5%, and the rate instruction of the program-controlled infusion pump 16 is 0, i.e., keeping the original rate;

$0.2 <$ default free calcium concentration in the venous line blood of the blood purification machine (mmol/L)$< 0.35$, wherein the pump speed instruction of the program-controlled infusion pump 17 is 0, and the rate instruction of the program-controlled infusion pump 16 is 0, i.e., keeping the original rate.

(4) When the second laboratory analysis data falls within the basic data range, the program control portion 15 will issue an operation maintenance signal to the program-controlled infusion pump 16 and the program-controlled infusion pump 17;

This program database:
$1.1 \times 0.96 <$ calculated value of free calcium concentration in peripheral venous blood (mmol/L)$< 1.3 \times 0.96$, or with the changes as mentioned in above (1)-(3), wherein the pump speed instruction of the program-controlled infusion pump 17 is 0, that is, keeping the original rate, or corresponding to the instructions for the above changes (1)-(3), and the rate instruction of the program-controlled infusion pump 16 is 0, i.e., keeping the original rate;

$0.2 <$ default free calcium concentration in the venous line blood of the blood purification machine (mmol/L)$< 0.35$, wherein the pump speed instruction of the program-controlled infusion pump 17 is 0, and the rate instruction of the program-controlled infusion pump 16 is 0, i.e., keeping the original rate.

(5) When the second laboratory analysis result is higher than the basic data range, the program control portion 15 will send an instruction the program-controlled injection pump 16 to increase the corresponding citrate supply rate;

This program database:
$1.1 \times 0.96 <$ calculated value of free calcium concentration in peripheral venous blood (mmol/L)$< 1.3 \times 0.96$, or with the changes as mentioned in above (1)-(3), wherein the pump speed instruction of the program-controlled infusion pump 17 is 0, that is, keeping the original rate, or corresponding to the instructions for the above changes (1)-(3), and the rate instruction of the program-controlled infusion pump 16 is 0, i.e., keeping the original rate;

$0.4 <$ default free calcium concentration in the venous line blood of the blood purification machine (mmol/L)$< 0.5$, wherein the pump speed instruction of the program-controlled infusion pump 17 is 0, and the rate instruction of the program-controlled infusion pump 16 increases 5%.

(6) When the second laboratory analysis result is lower than the basic data range, the program control portion 15 will send an instruction the program-controlled injection pump 16 to reduce the corresponding citrate supply rate;

This program database:

$1.1 \times 0.96$<calculated value of free calcium concentration in peripheral venous blood (mmol/L)<$1.3 \times 0.96$, or with the changes as mentioned in above (1)-(3), wherein the pump speed instruction of the program-controlled infusion pump 17 is 0, that is, keeping the original rate, or corresponding to the instructions for the above changes (1)-(3), and the rate instruction of the program-controlled infusion pump 16 is 0, i.e., keeping the original rate;

$0.15$<default free calcium concentration in the venous line blood of the blood, purification machine (mmol/L)<$0.2$, wherein the pump speed instruction of the program-controlled infusion pump 17 is 0, that is, keeping the original rate, and the rate instruction of the program-controlled infusion pump 16 reduces 5%.

At the end of the treatment, the full-automatic regional citrate anticoagulation machine provided in the present invention automatically terminates the treatment and shuts down according to the program settings.

It should be noted that, for the foregoing method embodiment, for the sake of simplicity, it is described as a series of action combinations, but a person skilled in the art shall recognize that the present invention is not limited by the sequence of actions described. Thus, according to the present invention, certain steps may be performed in other sequence or at the same time. Secondly, it will be understood by a person skilled in the art that the embodiments described in the description are preferred embodiments and that the actions involved are not always necessary for the present invention.

The last thing to note is that: the foregoing embodiments are merely illustrative of the technical aspects of the present invention, rather than limiting thereof. Although the present invention has been described in detail with reference to the foregoing embodiments, it will be understood by those of ordinary skill in the art that, the technical solutions described in the foregoing embodiments can be modified or equivalently replaced with some of the technic& features thereof; all these modifications or substitutions do not depart from the spirit and scope of the technical solutions of the embodiments of the present invention.

The invention claimed is:

1. An automatic regional citrate anticoagulation machine comprising:
   a sampling portion having a connecting catheter, an air detector, a pressure sensor, a first peristaltic pump, and a blood sample storage purifier successively connected in series, said sampling portion adapted to extract a blood sample and to send the blood sample to the blood sample storage purifier for storage and purification;
   a sample injection portion having a second peristaltic pump, a sample injection tube and a sample loading slot, one end of the second peristaltic pump communicating with the first peristaltic pump, another end of the second peristaltic pump communicating with the sample injection tube, the sample injection tube being insertable into the sample loading slot, said sample injection portion adapted to convey the blood sample in the blood sample storage purifier to the sample loading slot through a sample injection portion channel;
   an assay and analysis portion having a sample suction tube and an analyzer, one end of the sample suction tube being inserted in the sample loading slot, and other end of the sample suction tube being connected to the analyzer, the sample suction tube adapted to convey the blood sample in the sample loading slot to the analyzer for blood sample analysis;
   a program control portion connected to said sample injection portion and said assay and analysis portion, the program control portion controlling said sampling portion and said sample injection portion and said assay and analysis portion so as to compare data results by the analyzer; and
   an administration portion connected to said program control portion so as to receive instructions relative to the compared data results.

2. The automatic regional citrate anticoagulation machine of claim 1, wherein said administration portion has a first connecting tube, one end of the first connecting tube being connected to an arterial-end line inlet, another end of the first connecting tube being connected to a program-controlled infusion pump, the program-controlled infusion pump adapted to pump a citrate solution into the arterial-end line inlet via the first connecting tube, said administration portion having a second connecting tube, one end of the second connecting tube being connected to a venous-end line inlet, another end of the second connecting tube being connected to the program-controlled infusion pump.

3. The automatic regional citrate anticoagulation machine of claim 1, wherein the connecting catheter having an arterial line connecting catheter and a venous line connecting catheter, the arterial line connecting catheter and the venous line connecting catheter being connected to the passage of said sampling portion through a two-position three-way valve and communicate with the air detector, a front end of the air detector having a first cut-off clamp thereon, the first pressure sensor and the second peristaltic pump having a second cut-off clamp therebetween, the blood sample storage purifier being connected to a second pressure sensor and to a bottle, the blood sample storage purifier and the second pressure sensor having a third cut-off clamp therebetween, the bottle having a liquid therein, the bottle cooperating with the second pressure sensor and adapted to clean the passage of said sampling portion.

4. The automatic regional citrate anticoagulation machine of claim 1, wherein said sample injection portion communicates with the blood sample storage purifier.

5. The automatic regional citrate anticoagulation machine of claim 1, wherein said sample injection portion further comprises a liquid collector and a sample injection tube cleansing utensil connected in said sample injection portion through a manipulator.

6. The automatic regional citrate anticoagulation machine of claim 1, wherein said program control portion comprises a computer and a PLC.

7. The automatic regional citrate anticoagulation machine of claim 1, wherein the analyzer is adapted to monitor at least one indicator in electrolytes, blood glucose, parathyroid hormone, adrenal hormone, pH value and citrate circulation.

8. The automatic regional citrate anticoagulation machine of claim 1, wherein said program control portion is adapted to decide an administration state of said administration portion relative to the compared results.

* * * * *